United States Patent [19]
Lange et al.

[11] Patent Number: 5,936,247
[45] Date of Patent: Aug. 10, 1999

[54] IMAGING ATTENUATION CORRECTION MECHANISM

[75] Inventors: Kai Lange, Vedbaek; Jørn-Erik Jensen, Horsholm, both of Denmark

[73] Assignee: General Electric Company, Milwaukee, Wis.

[21] Appl. No.: 08/884,048

[22] Filed: Jun. 27, 1997

[51] Int. Cl.⁶ .................................................. G01T 1/166
[52] U.S. Cl. .............................. 250/363.03; 250/363.04
[58] Field of Search ........................... 250/363.04, 363.03

[56] References Cited

U.S. PATENT DOCUMENTS 5,376,795  12/1994  Hasegawa et al. ................. 250/363.04
5,629,971   5/1997  Jones et al. ........................... 378/145

*Primary Examiner*—Constantine Hannaher
*Attorney, Agent, or Firm*—Quarles & Brady, LLP

[57] ABSTRACT

An apparatus for generating gamma transmission and gamma emission images simultaneously including two emission cameras disposed on opposite sides of an imaging area so as to oppose each other, a gamma line transmission source and a line detector positioned between the two emission cameras on opposite sides of the imaging area, at least one of the source or line detector being movable along a path that substantially traverses the distance between the two emission cameras. The two emission cameras, line source and line detector are all secured to the same gantry for rotation about the imaging area so that transmission and emission images can be generated simultaneously.

15 Claims, 6 Drawing Sheets

IMAGING ATTENUATION CORRECTION MECHANISM

BACKGROUND OF THE INVENTION

The present invention relates to medical imaging cameras and more specifically to an imaging system including a mechanism for determining emission attenuation for compensating emission images for varying patient densities.

Single photon emission computed tomography (SPECT) examinations are carried out by injecting a dilution marker comprising a compound labeled with a radiopharmaceutical into the body of a patient to be examined. A radiopharmaceutical is a substance that emits photons at one or more energy levels. By choosing a compound that will accumulate in an organ to be imaged, compound concentration, and hence radiopharmaceutical concentration, can be substantially limited to an organ of interest. A radiopharmaceutical that emits photons or gamma emissions at a single known energy level is chosen.

While moving through a patient's blood stream the marker, including the radiopharmaceutical, becomes concentrated in the organ to be imaged. By measuring the intensity of the photons emitted from the organ, organ characteristics, including irregularities, can be identified.

To measure photon intensity a planar gamma camera is used. A gamma camera consists of a stand that supports a collimator, a scintillation crystal and a plurality of photomultiplier tubes (PMTs) in a single position with respect to a patient. The collimator typically includes a lead block with tiny holes therethrough which define preferred photon paths. The preferred paths are usually unidirectional and perpendicular to the length of the collimator. The collimator blocks emissions toward the crystal along non-preferred paths.

The scintillation crystal is positioned adjacent the collimator on a side opposite the patient. The crystal absorbs photons that pass through the collimator on a front surface and emits light from a back surface each time a photon is absorbed.

The PMTs positioned adjacent the crystal and on a side of the crystal opposite the collimator. Light emitted by the crystal is detected by the PMTs which in turn generate analog intensity signals.

A processor receives the PMT signals and digitally stores corresponding information as an M by N array of elements called pixels. The values of M and N are commonly 64 or 128 pixels across the two dimensions of the image. Together the array of pixel information is used by the processor to form an emission image corresponding to the specific camera position.

Most gamma camera systems generate a plurality of emission images, each taken by positioning the detector parallel to, and at an angle about, a rotation axis. The angle is incremented between views so that the plurality of images can be used together to construct pictures of transaxial slices of the body using algorithms and iterative methods that are well known to those skilled in the tomographic arts.

Unfortunately, because different materials are characterized by different attenuation coefficients, photons are attenuated to different degrees as they pass through different portions of a patient's body. For example, an inch of bone will typically attenuate a greater percentage of photons than an inch of tissue. Similarly, air filled space in a lung or sinus cavity will attenuate less photons than a comparable space filled with tissue or bone. In addition, photons passing through four inches of tissue will be attenuated to a greater degree than photons passing through one inch of tissue. Thus, if an organ emitting photons is located on one side of a patient's body, photon density on the organ side of the body will typically be greater than density on the other side.

Non-uniform attenuation about the organ causes emission image errors. For example, non-uniform attenuation causes artifacts in resulting images which can obscure images and reduce diagnostic effectiveness.

Attenuation caused by different body structures can be compensated for by generated a body attenuation map and using the attenuation map to correct emission images. An attenuation map is a map which clearly indicates attenuation characteristics of different portions of a patient's body. For example, a map for the chest area would indicate little attenuation in an air filled lung cavity, relatively greater attenuation in the chest muscle and still greater attenuation in rib and spinal bone sections.

In order to obtain an accurate attenuation map, a transmission imaging process is performed. In transmission imaging, body attenuation is directly measured by using transmission computed tomography techniques wherein a radiation source is used to project photons or the like through a patient's body. Radiation that is not attenuated is received by a scintillation crystal/detector on the opposite side of the patient. As with emission imaging, in transmission imaging, the source and detector are rotated about the patient to generate transmission images corresponding to a multiplicity of angles. The transmission images are reconstructed into the attenuation map using conventional tomography algorithms.

By collecting data corresponding to the intensity of the photon emissions and the intensity of the photon transmissions through the patient at the same gantry angles, a computer system uses the non-uniform attenuation map to correct emission images collected during emission studies.

Two different techniques have been used to obtain both transmission and emission images and are referred to herein as consecutive and simultaneous techniques. According to the consecutive technique, transmission images are generated either prior to or after generating emission images to generate an attenuation map that can be used to compensate for attenuation variations in later generated emission images.

Consecutive techniques have two main shortcomings. First, by generating transmission images prior to generating emission images, scan time required to generate all necessary images is approximately doubled. Second, when an attenuation map is used to compensate for attenuation variations in emission images, if patient position changed between the time when the transmission images were generated and the emission images were generated, the transmission and emission images will not correlate and the attenuation map will be useless for the purpose of compensating for non-uniform attenuation.

According to the simultaneous technique, both transmission and emission images are generated simultaneously. This technique is preferred because it is fast and the correlation problem associated with the consecutive data gathering techniques is eliminated.

Even though simultaneous imaging techniques increase imaging speed, imaging requires a relatively long period which can both cause patient discomfort and result in erroneous imaging data. In order to minimize patient exposure to radiation, the radiopharmaceutical attached to the compound marker and injected into a patient's bloodstream typically has relatively low photon emission levels. As a result, each emission image requires an appreciable amount of time (e.g. 40 seconds) to generate. Typically, to generate sufficient data to form useable tomographic images, at least 64 views equi-spaced about the 360° surrounding a patient will be generated. With 64 views generated by a single camera, an entire imaging process can take longer than 40 minutes to complete. To increase image quality by reducing image granularity, the total number of images can be increased. If the number of images is doubled to 128, required imaging time can be nearly one and one-half hour.

Despite requiring an appreciable amount of tomography machine time which in and of itself is objectionable because it reduces patient throughput, prolonged imaging periods cause patients discomfort as a patient has to remain nearly completely still during the entire imaging procedure. During 40 minute or more procedures it is difficult if not impossible for most patients to remain completely still. When a patient moves, resulting images are distorted and blurred and once again, healthy tissue can be mistaken for irregular tissue or vice versa. For these reasons any method to speed up imaging without reducing accuracy is advantageous.

To increase imaging speed, many systems now employ two or more gamma cameras positioned around an imaging area to generate two or more emission images simultaneously. For example, referring to FIG. 1, one system includes two cameras 10,12 separated by a 90° angle about a rotation axis. Here, both cameras 10, 12 are used for emission imaging and one of the two cameras is simultaneously used for transmission imaging with a transmission source (not shown) positioned opposite the camera providing photons at an energy level appreciably different than the emission energy levels. The emission/transmission camera collects both emission and transmission photons, identifies the different photon energy levels and generates transmission data simultaneously.

This solution has a number of shortcomings. First, a second emission camera appreciably increases system costs as scintillation crystals and PMT arrays are relatively expensive imaging components.

Second, with this solution, if imaging is required from angles throughout 360° about the rotation axis, the cameras have to be rotated through 270° and imaging time is reduced by only 25% with a total camera cost for the two cameras that is 100% greater than a single camera.

Third, referring again to FIG. 1, to reduce stray radiation within an imaging room, gamma cameras 10,12 typically include a radiation receiving boot 14,16 which extends laterally therearound. When two cameras 10,12 are oriented at 90° about a rotation axis, the boots 14,16 interfere at a common edge and an area 18 adjacent thereto within an imaging area 20 cannot be imaged. If an organ to be imaged is located within area 18, imaging information cannot be obtained without moving the patient to a different section of the imaging area 20. While this may be acceptable in some cases, in other cases, because the imaging area 20 must be kept as small as possible to maintain a relatively small system size (i.e. small gantry and small detectors), many patients cannot be moved to more than a few positions within the imaging area. Thus, with cameras spaced at 90° about the rotation axis, the effective imaging area 20 is substantially reduced.

Another solution to increase imaging speed is to provide three cameras and a single transmission source. Two of the cameras can be used to detect emission information and the third camera can be positioned opposite the transmission source to detect transmission information. In this case, if the three cameras are equispaced at 120° intervals around the rotation axis, images throughout the 360° about a rotation axis can be generated through 240° of rotation and imaging time can be reduced by 33%. However, this time savings comes at the expense of three cameras, three cameras having a cost which is 200% greater than the cost of a single camera.

Another three camera configuration includes two emission cameras positioned so as to oppose each other and a third transmission camera at 90° with respect to each of the emission cameras. In this case, 360° imaging can be provided by rotation through 180° and imaging time can be cut in half. Here, for the cost of three cameras, imaging time is reduced by 50%.

Unfortunately, while three camera systems increase speed appreciably, the costs associated with additional cameras and the transmission source cannot be justified in most cases.

Yet another solution would be to provide a line transmission source between one planar gamma camera and an imaging area wherein the line source directs gamma transmissions toward an opposed planer camera at an energy level different than the emission energy level. In this case, only two planer gamma cameras and a single line transmission source would be required thus reducing costs and still providing a fast system. With this configuration, imaging time would be reduced by as much as 50% and the two cameras would only cost twice as much as a single camera system.

Unfortunately, this configuration also has shortcomings. This configuration would cause at least one of the gamma cameras to be positioned a substantial distance away from the imaging area to accommodate the line source between the camera and the imaging area. Image quality decreases as the distance between an emission source (i.e. the radiopharmaceutical in an organ) and the camera increases. Thus, this solution would result in lower quality emission data.

Therefore, it would be advantageous to have a gamma camera system that can appreciably decrease imaging time, is relatively inexpensive and simultaneously provides both emission image data and transmission image data.

SUMMARY OF THE INVENTION

The present invention provides a gamma camera system including first and second opposed planar gamma cameras mounted to an annular gantry for rotation about a rotation axis, the two cameras defining an imaging area therebetween. The first and second cameras are positioned on first and second sides of the imaging area, respectively. A line detector is positioned on a third side of the imaging area between the two cameras and a gamma line transmission source is positioned opposite the line detector on a fourth side of the imaging area. Either the line source or the line detector is equipped so that it can move along a path which substantially traverses the distance between the two emission cameras, the source directing a line transmission toward the line detector at all times. Both the source and line detector are mounted on the same gantry as the two cameras and rotate therewith so that transmission images can be generated at the same time emission images are generated.

Thus, one object of the invention is to facilitate inexpensive and fast emission data gathering. To this end, only two planar emission cameras are used and positioned so as to oppose each other. The two cameras only require two photomultiplier tube arrays and associated equipment and can provide 360° imaging during only 180° of rotation.

Another object is to generate both emission and transmission data simultaneously. While the two cameras are generating emission data, the line detector and source together generate transmission data that can later be used to compensate for non-uniform attenuation in emission images.

Yet another object is to generate both emission and transmission data simultaneously and inexpensively without degrading emission data. With the inventive configuration, emission data is gathered using a relatively inexpensive line source and line detector instead of planar elements. In addition, because the source and line detector are not positioned between either camera and the imaging area, emission data is not degraded due to camera distance.

In one embodiment either the source or line detector is stationary and the apparatus further includes an aligner for rotating the source as the moving component is moved along the path so as to direct the line transmission toward the line detector at all times.

In one aspect the line detector is positioned parallel to the axis of gantry rotation, the first and second detectors are centered along an imaging axis perpendicular to the axis of rotation and the line detector is positioned along an axis that makes a 90 degree angle with the imaging axis.

In another embodiment the line detector is perpendicular to the axis of rotation and substantially traverses the distance between the first and second detectors.

Preferably both the third detector and the source are secured to the gantry for rotation with the first and second detectors.

In another embodiment both of the source and line detector are moveable and the motivator is capable of moving one or both of the source and line detector. The invention also includes a method to be used with the apparatus described herein.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVENTION

A. Hardware Configuration

Figure 1:
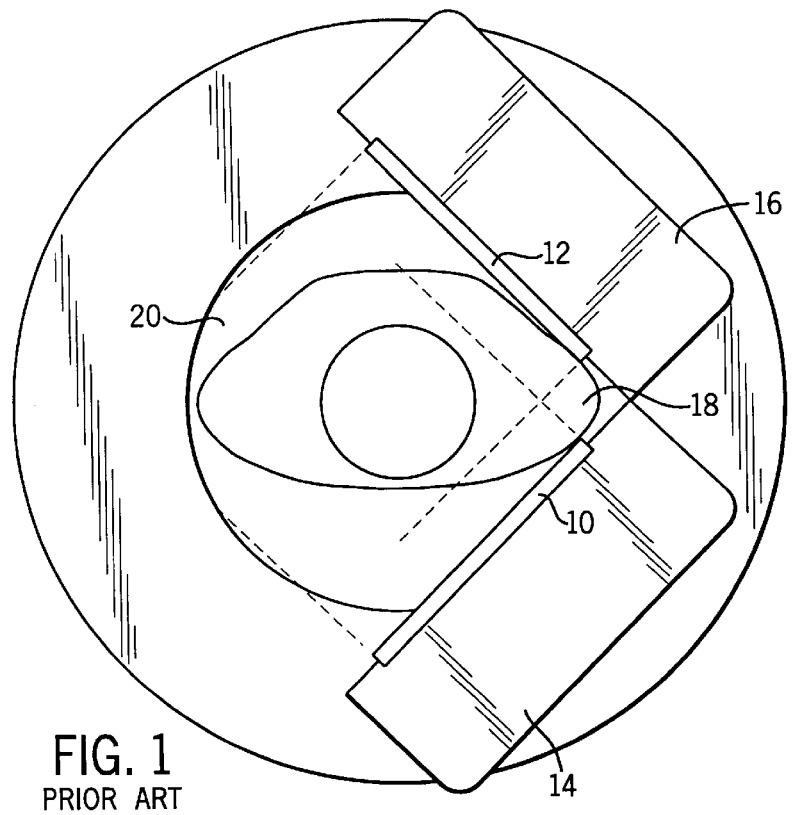
FIG. 1 is a plan view of a prior art gamma camera configuration.
Figure 2:
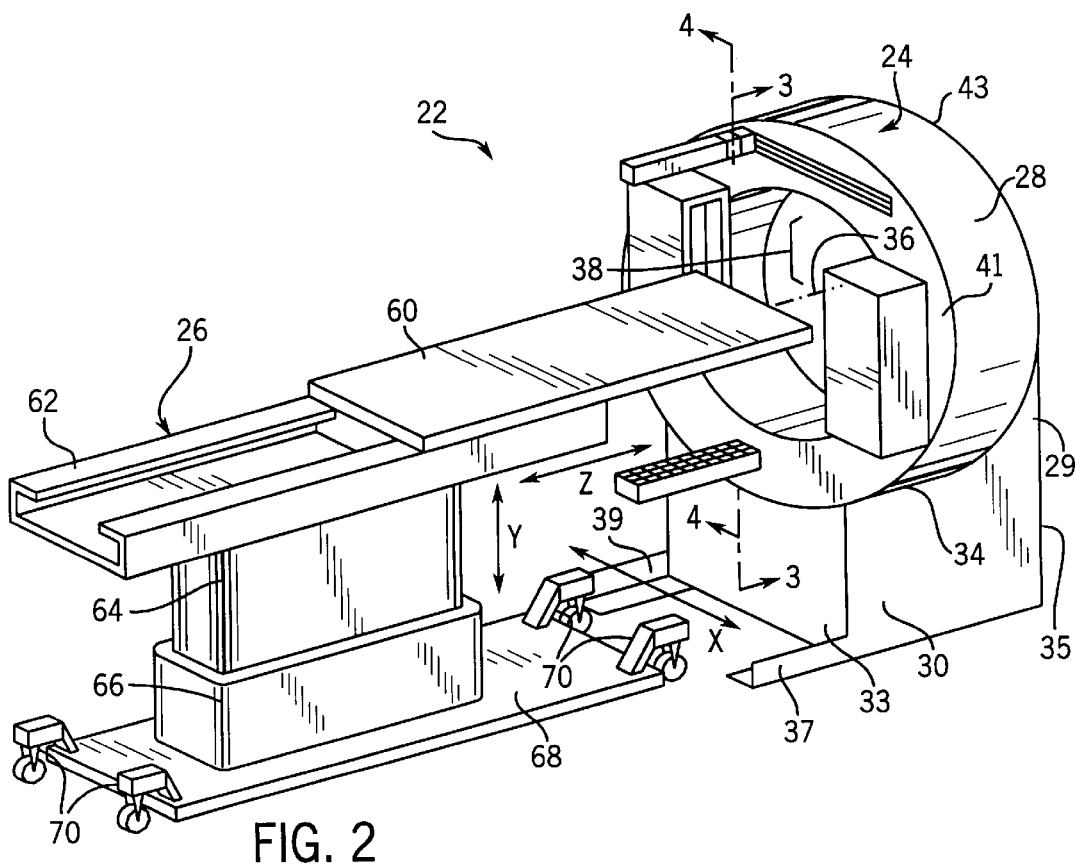
FIG. 2 is a perspective view of an imaging system employing the present invention.

Referring now to the drawings, wherein like reference numerals represent corresponding elements throughout the several views, and more specifically, referring to FIG. 2, there is shown, generally at 22, an imaging system including a tomography machine 24 and a patient support table 26.

The support table 26 includes a top surface 60 interleaved to a lower bracket member 62 which allows supported movement of the top surface 60 along a horizontal Z-axis. The bracket member 62 is supported by a vertical leg 64 which extends upwardly from a collar 66. The length of leg 64 can be increased or decreased to raise or lower top surface 60 along a vertical Y-axis. Collar 66 is secured to a planar dolly 68 having four wheels collectively identified by the numeral 70, one wheel 70 attached at each of four corners. The wheels 70 allow an operator to move the entire table 26 laterally along an X-axis or along the Z-axis. Thus, the table 26 allows an operator to move the top surface 60 and a patient thereon within a range of three dimensional space.

The tomography machine 24 includes a pedestal 30, a gantry 28, two planar gamma cameras 32, 34, a gamma transmission line source 48 and a gamma transmission line detector 50. The pedestal 30 has a front end 33 and a back end 35 and includes two stabilizing legs 37, 39 which extend forward from the front end 33, distal ends of the legs 37, 39 contacting a ground surface in front of the pedestal to stabilize the pedestal front end 33 as the tomography machine 24 is generally front end heavy. The top surface of the pedestal 30 is generally shaped concavely upward so as to receive an outer surface of gantry 28. In addition, although not shown, the pedestal 30 may also house a gantry motor for rotating the gantry 28 about a central gantry rotation axis 36.

The gantry 28 is generally doughnut shaped about the central rotation axis 36. The pedestal 30 supports the gantry 28 in an upright vertical orientation so that its rotation axis 36 is horizontal and can be parallel to the support table Z-axis. The gantry 28, like the pedestal 30, has a front end and a back end defined by front and back surface 41 and 43, respectively. The gantry 28 ideally can rotate about central rotation axis 36 through 540° of rotation and, at a minimum, to produce 360° imaging, must be able to rotate through 180°.

Figure 3:
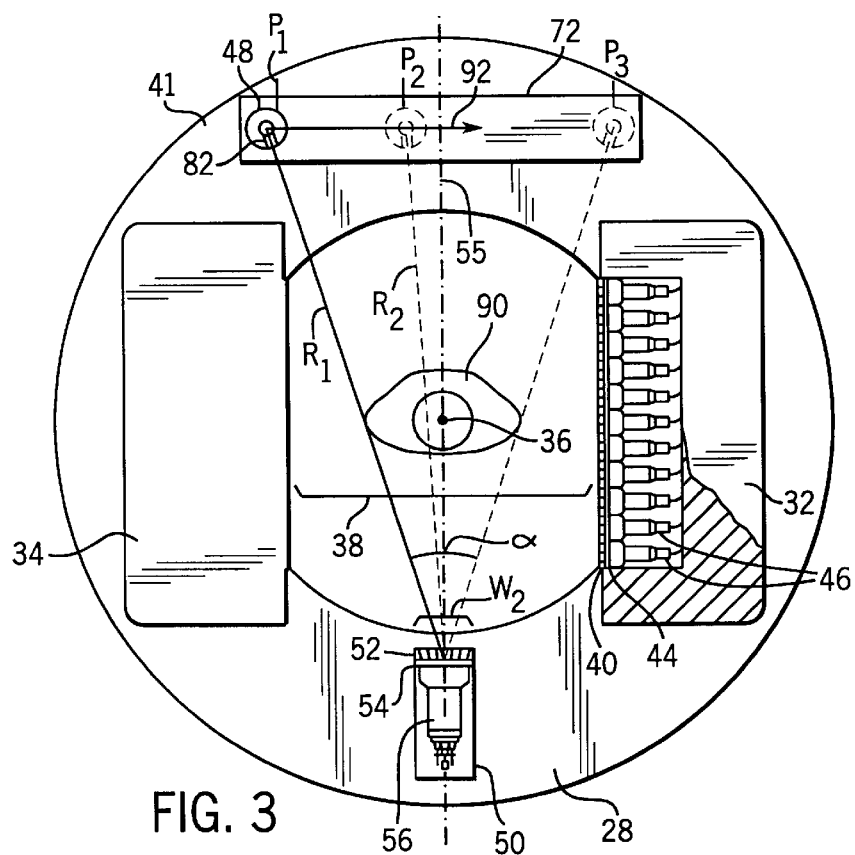
FIG. 3 is a plan and view taken along the line 3—3 of FIG. 2.

Referring to FIGS. 2 and 3, the two gamma emission cameras 32, 34 are mounted securely to the front surface 41 of the gantry 28 so that when the gantry 28 rotates about axis 36, the cameras 32, 34 likewise rotate. Importantly, the two cameras 32, 34 are mounted so as to directly oppose each other on opposite sides of an imaging area 38 therebetween.

The gamma cameras 32, 34 are used to detect and identify coordinates of gamma emissions. Each camera 32, 34 includes a lead plate 40 that defines a myriad of fine holes perpendicular to its length so that the plate acts as a collimator defining parallel paths therethrough. A scintillation crystal 42 is positioned behind each collimator 40 which absorbs gamma emissions which pass through the collimator holes perpendicular to the collimator's length and produce light emissions corresponding to each absorbed gamma emission. The light emissions are directed toward an array of closely packed PMTs which are collectively designated by numeral 46.

Figure 4:
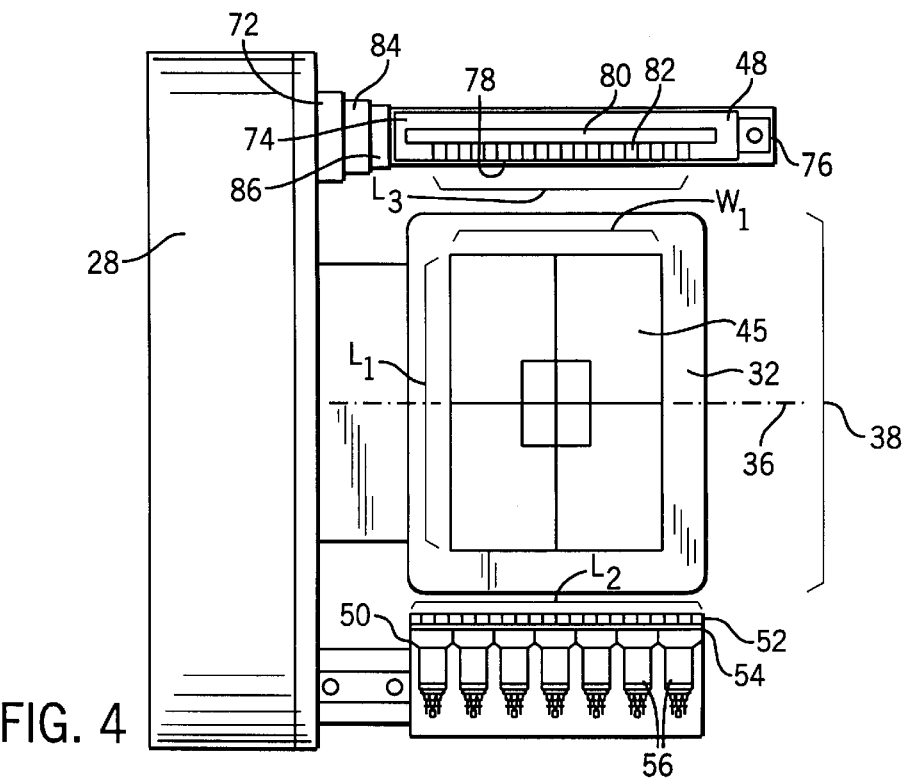
FIG. 4 is a plan and view taken along the line 4—4 of FIG. 2.

Detected light emissions cause the PMTs 46 to produce analog signals which are sent to a processor (not shown) that uses the signals to compute M and N coordinates of each gamma emission absorbed in terms of analog signal magnitudes. Referring also to FIG. 4, each of the cameras 32, 34 has a planar imaging surface 45 with a length $L_1$ and a width $W_1$ so that an entire area as opposed to a single line can be imaged at one time. The cameras 32, 34 are equispaced from an imaging axis 55 which intersects the rotation axis 36.

Computing the M and N coordinates in terms of analog signals is well known. One scheme for determining the M and N coordinates of each gamma emission is described in U.S. Pat. No. 4,142,102 which is incorporated herein by reference. The analog M and N coordinate signals are then used at a later time to generate an emission image corresponding to the collected data. One scheme for generating emission images is described in U.S. Pat. No. 5,337,213 which is incorporated herein by reference.

Referring to FIGS. 2, 3 and 4, the line source 48 and line detector 50 are also mounted to the front surface 41 of the gantry 28. The line source 48 and detector 50 are mounted between the two gamma cameras 32, 34 on opposite sides of the imaging area 38. Preferably, the line detector 50 is oriented so as to define a 90° angle with the imaging axis 55. In FIGS. 2, 3 and 4 the line source is mobile and detector 50 is stationary with respect to the gantry 28.

Referring to FIGS. 3 and 4, the line detector 50 is constructed like each of the two cameras 32, 34 and includes a collimator 52, a scintillation crystal 54, and a plurality of PMTs collectively identified by numeral 56. Importantly, however, detector 50 is a line detector, not a planar detector. Thus, instead of including a full two dimensional array of PMTs and an associated planar collimator and scintillation crystal, detector 50 preferably includes a single row of PMTs 56 and a correspondingly narrow crystal 54 and collimator 52. In many cases the line detector 50 will have 64 or even 128 times fewer PMTs than a typical gamma camera (i.e. many gamma cameras have 64×128 or 128×128 PMT arrays). For this reason, the line detector 50 represents a substantial hardware savings over planar cameras 32, 34. Preferably the line detector 50 extends perpendicular to, and from the front surface 41 of, the gantry 28 so that its length $L_2$ is parallel to the width $W_1$ of camera 32.

Referring to FIG. 4, along the length $L_2$ of line detector 50, paths through the collimator 52 are perpendicular to the scintillation crystal 54 but, referring also to FIG. 3, along the width $W_2$ of the detector 50 paths through the collimator 52 form a fan configuration about the imaging axis 55 so that line transmissions from source 48 will pass through the collimator 52 despite varying angles of the source 48.

Referring to FIGS. 2, 3 and 4 the line source 48 has a proximal end 74, a distal end 76, a transmission surface 78, and a length $L_3$. The source 48 includes a gamma or photon transmitting element 80 and a collimator 82 which only allows gamma transmissions to exit the transmission surface 78 in a direction perpendicular to the source length $L_3$. The transmission element 80 is chosen so that it emits a line transmission including gamma particles at an energy that is appreciably different than the energy level of the photon emissions produced by the radiopharmaceutical. The source 48 is mounted at its proximal end 74 for movement along a track 72 between the two gamma cameras 32, 34 on the side of the imaging area 38 opposite the line detector 50. When mounted, the transmission surface 78 is parallel to the detector collimator length $L_2$ and is directed across the imaging area 38 toward detector 50.

The track 72 is perpendicular to, and centered along, the imaging axis 55 and substantially traverses the distance between the two cameras 32, 34.

The source 48 includes a motivator or first motor 84 at its proximal end which can be used to move the source 48 along the track 72 in a controlled manner. In addition, the source 48 includes an aligner or second motor 86 which can rotate the collimator 82 through an arc α to change the direction of the line transmission as a function of source position on the track 72. For example, referring to FIG. 3, the source 48 is shown in a first position $P_1$ and two other positions $P_2$ and $P_3$ (in phantom). In each case, because the line detector 50 does not move in this embodiment, the transmission line direction must be adjusted to direct the line transmission toward the detector 50. Thus, at position $P_1$ the source is directed along line $R_1$, at position $P_2$ the direction is along line $R_2$, and so on.

Referring to FIG. 4, the source 48 and detector 50 lengths $L_3$, $L_2$, respectively, each are preferably equal to or slightly greater than the width $W_1$ of camera 32.

B. Operation

In operation, after a suitable radiopharmaceutical has been injected into a patient's blood stream, with the patient (generally 90) resting on top surface 60, the table 26 is manipulated along the X and Y axes until the patient 90 is positioned generally concentrically with the gantry along rotation axis 36. The patient 90 and table 26 are then manipulated along the rotation axis 36 in the Z-axis direction until the portion of the patient to be imaged is located between the two planar gamma cameras 32, 34 within the imaging area 38. When properly positioned, the table 26 is locked in place so that it will not move with respect to the tomography machine 24 during imaging.

After the time required for the radiopharmaceutical to become concentrated in the organ to be imaged, the imaging process is begun. During imaging, both emission and transmission data required to generate emission and transmission images is generated for a plurality of angles about the patient 90. Two sets of emission data are simultaneously generated, a separate set of emission data generated by each of the two gamma cameras 32, 34. At each imaging angle, it takes approximately 40 seconds to generate sufficient emission data to form an image.

At the beginning of each emission imaging period at each imaging angle, the line source 48 is positioned at one end of the track 72 and the collimator 82 is oriented so that the line transmission from source 48 is directed toward detector 50. For the purpose of this explanation it will be assumed that the source 48 is positioned at the left-hand side of the track 72 at the beginning of each imaging period as illustrated in FIG. 3.

Referring to FIGS. 3 and 4, during an imaging period, the first motor 84 operates to move the source 48 along the track 72 from the left-hand side to the right-hand side in the direction indicated by arrow 92. In addition, as the source 48 is moved from position $P_1$ to position $P_3$ the second motor 86 is controlled, as a function of source 48 position on track 72, to rotate the collimator 82 so that gamma transmissions emanating from the source 48 are directed toward detector 50 at all times.

At the end of an imaging period three dimensional transmission data for the imaging angle through α has been generated. In addition, two sets of emission data have been generated, one set for each camera 32, 34. At this time the source 48 is momentarily turned off while the entire gantry 28, including cameras 32 and 34, detector 50 and source 48, is rotated about central rotation axis 38 to the next imaging angle. While the gantry 28 is rotating to the next imaging angle, the first motor 84 moves the source back to its original position $P_1$ at the right-hand side of track 72 while the second motor 86 repositions the collimator 82 in its original position.

Once the gantry 28 reaches the next imaging angle, the process begins again with the cameras 32, 34 generating separate emission data and the source 48 and detector 50 cooperating to generate and store transmission data for the next angle.

With the present configuration the gantry 28 only has to be rotated through 180° in order to generate 360° of emission transmission data. Each camera 32, 34 detects 180° of emission data while the line detector 50 effectively detects 360° because opposite detector angles (e.g. 0° and 180° or 45° and 225°) generate identical transmission data.

Once all the emission and transmission data has been generated and stored, a computer can be used to form both initial emission images and corresponding initial transmission images using iterative algorithms that are well-known in the art. After initial images have been developed, the initial transmission images can be used to generate an attenuation map indicating non-uniform attenuation. Next, the processor can use both the initial emission images and the attenuation map to compensate the initial emission images for non-uniform attenuation throughout the imaged portion of the patient's body to generate corrected emission images. Methods and apparatus for combining emission images and attenuation maps are well known in the art and therefore will not be explained in detail here. Any method for combining emission and attenuation data may be used. Then, the corrected emission images can be combined by a computer to provide accurate tomographic images of the imaged organ.

C. Other Embodiments

Figure 5:
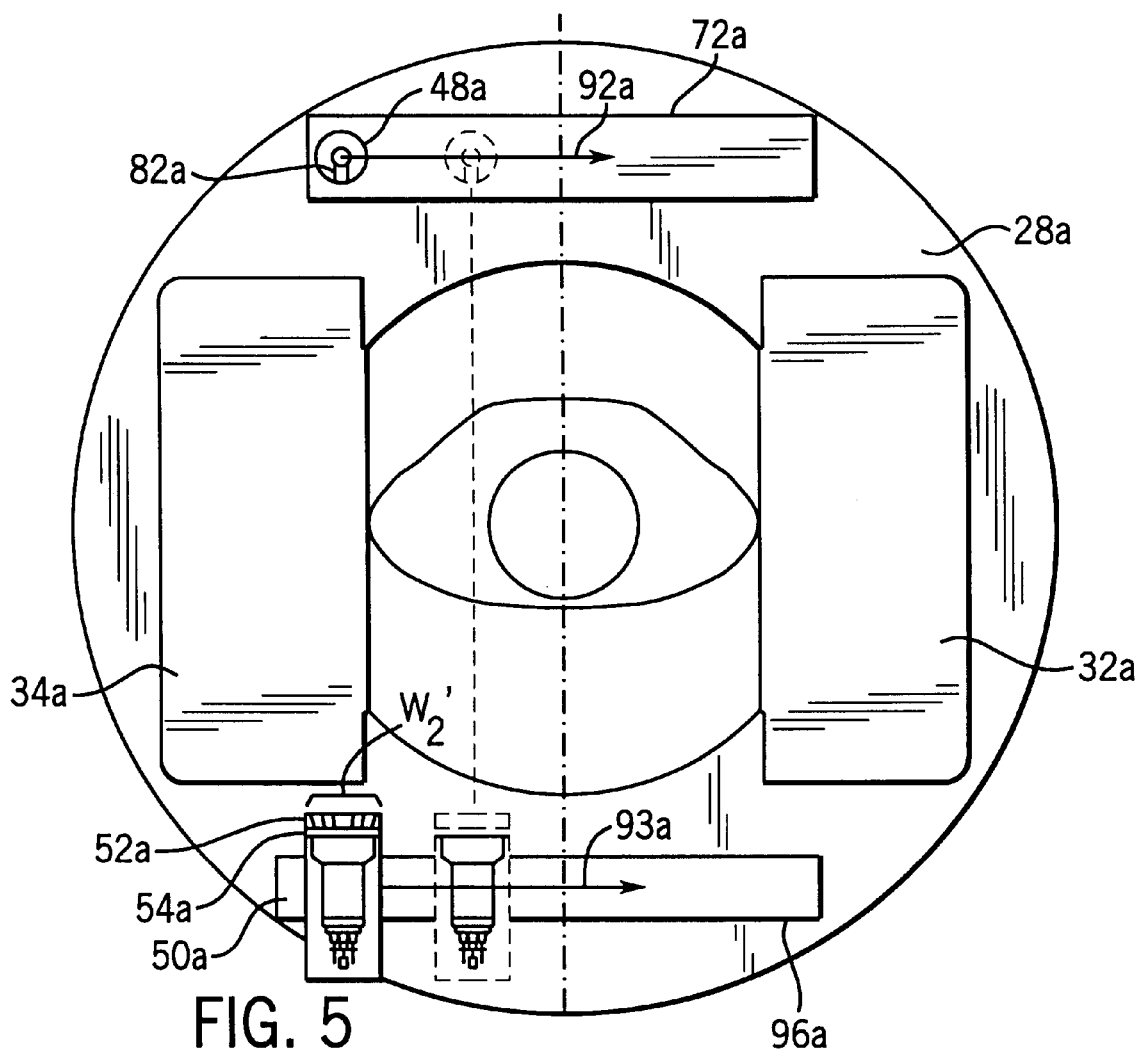
FIG. 5 is a plan view similar to the view of FIG. 3 of a second embodiment of the present invention.

Referring now to FIG. 5, a second embodiment of the present invention is illustrated wherein elements that are identical to the elements shown in the first embodiment are identified by like reference numerals with an "a" thereafter. In this embodiment, the gantry 28a, pedestal (not shown), and the two cameras 32a and 34a are identical to components described above. However, the line source 48a and line detector 50a are slightly different. Importantly, for the purposes of the present invention, both the source 48a and detector 50a are still inexpensively configured in that each has a general line configuration thus reducing the overall components required to provide transmission imaging. However, in this embodiment, both the line detector 50a and line source 48a are mounted to separate parallel tracks 96a, 72a, respectively, each of which substantially traverses the distance between the two opposing cameras 32a, 34a. In addition, in order to move the detector 50a along track 96a, the detector 50a includes a motivator or motor (not shown) at a distal end which connects to the track 96a. The motor moves the detector 50a at the same speed as the line source 48a along track 96a in the direction indicated by arrow 93a. Furthermore, the detector collimator 52a does not have a fan configuration but rather, provides paths therethrough along its width $W_2'$ which are perpendicular to the scintillation crystal 54a below the collimator 52a.

With respect to the line source 48a, in this embodiment there is only one motor associated with the line source 48a which moves the line source along the track 72a in the direction indicated by arrow 92a. The second motor, which was required in the first embodiment to rotate the collimator as a function of the position of the source on the track, is not needed in this embodiment.

With this second embodiment, during imaging periods, both the source 48a and the line detector 50a are initially positioned so as to oppose each other at similar ends of their corresponding tracks. Again, for the purposes of this explanation, it will be assumed that at the beginning of each imaging period both the source 48a and line detector 50a are initially positioned at the left-hand side of their respective tracks as illustrated in FIG. 5.

During each imaging period, while the gamma cameras 32a and 34a are receiving emission data, both the line source 48a and line detector 50a move together in an indexed fashion along their respective tracks from the left-hand side to the right-hand side collecting transmission data along the way. At the end of an imaging period, the source 48a is turned off and while the gantry 28a is rotated to the next imaging angle, both the source 48a and line detector 50a are moved back to their original positions at the left-hand side of their respective tracks. This process continues until all required emission data and transmission data has been generated.

Figure 6:
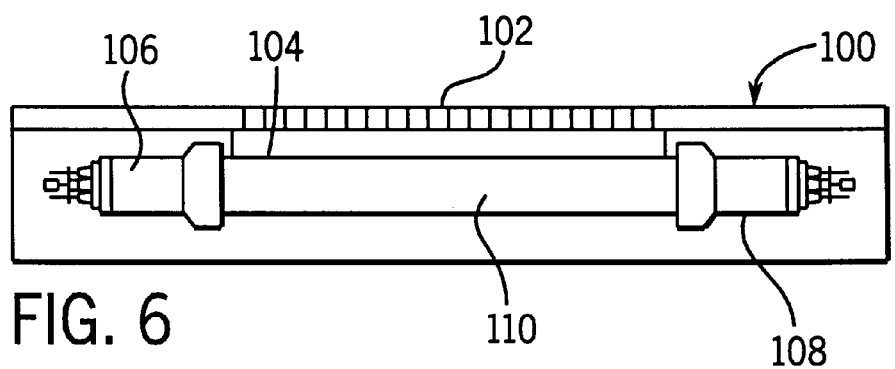
FIG. 6 is a plan view of a preferred line detector.

Referring now to FIG. 6, a second embodiment of the preferred line detector is illustrated. This line detector 100 is similar to the detector 50 shown in FIG. 4 in that it includes a collimator 102 and a scintillation crystal 104. This detector is different, however, because, instead of including a large number of PMTs, this detector only includes a single PMT with two signal generating ends 106, 108. In this case, when a gamma emission passes through the collimator 102 it is absorbed by the scintillation crystal 104 and light is emitted in the direction of single tube 110. Wherever the light is emitted along the crystal 104, it impacts the tube 110 in an adjacent location and causes two signals to be generated, one signal at end 106 and a second signal at end 108. The intensities of the signals at ends 106 and 108 is dependant upon the location of the emitted light. For example, if the emitted light is located closer to the left end 106 than the right end 108, the intensity of the signal generated at end 106 will be greater than the intensity at end 108 and visa versa. Thus, the line detector 100 illustrated in FIG. 6 is even less expensive than the detector shown in FIG. 4, and if used in the present invention, further reduces transmission imaging costs.

Figure 7:
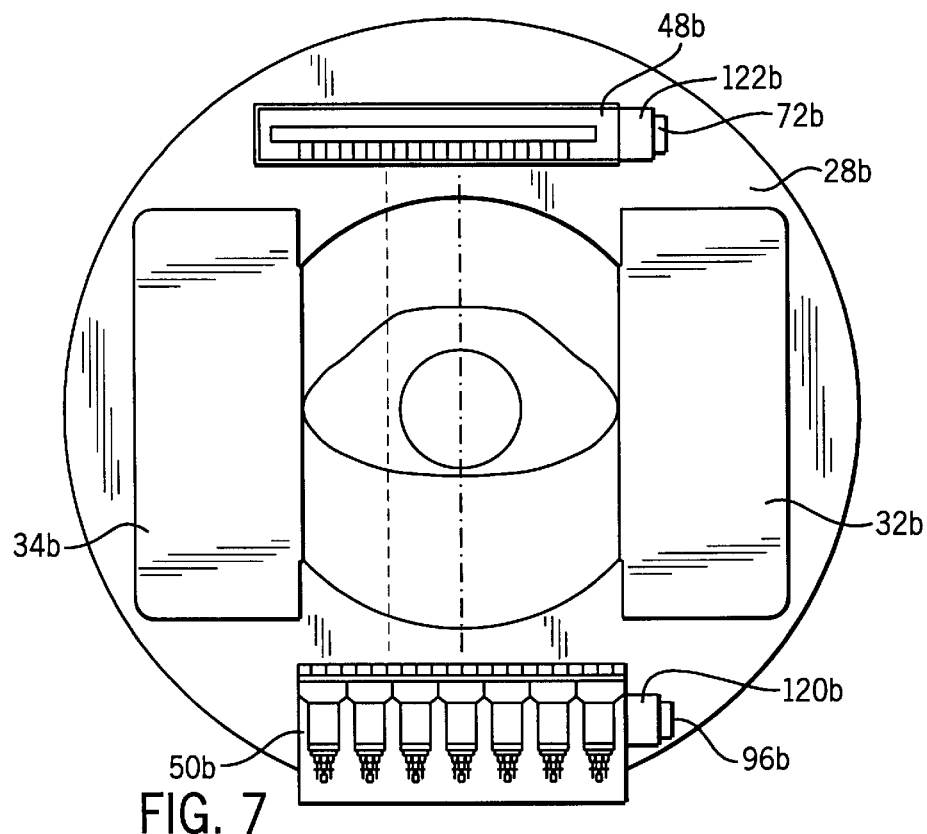
FIG. 7 is a plan view similar to FIG. 3 of a third embodiment of the present invention.
Figure 8:
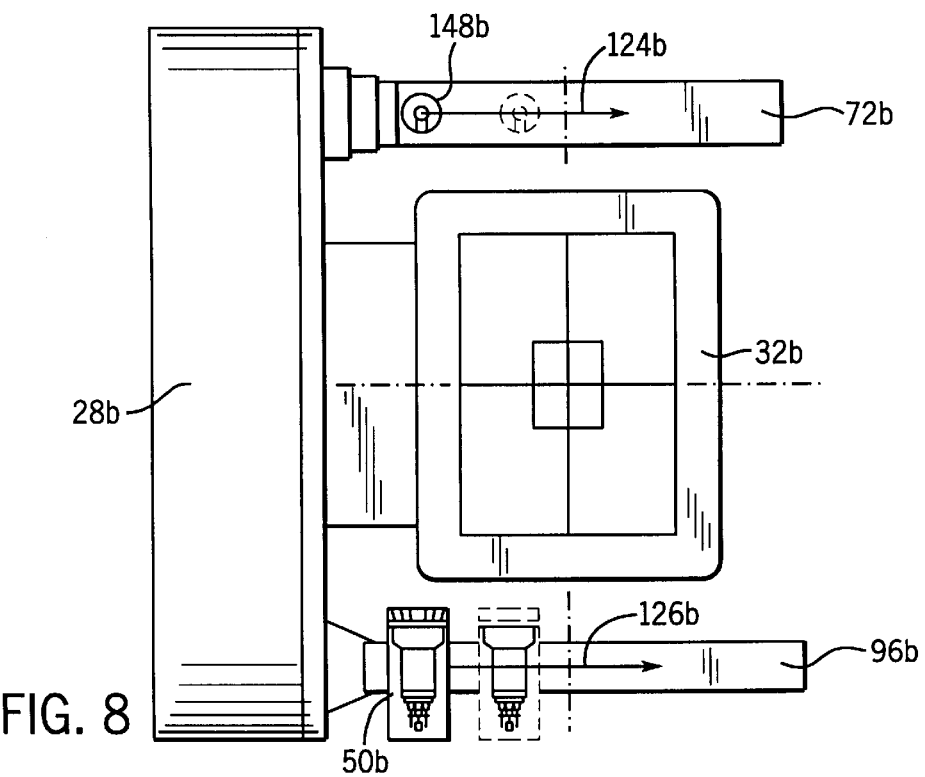
FIG. 8 is a plan view similar to the view of FIG. 4 of the third embodiment of the present invention.

Referring to FIGS. 7 and 8, a third embodiment of the invention is illustrated wherein elements identical to the elements shown in the first embodiment are identified by like reference numerals with a "b" thereafter. In this embodiment the two cameras 32b and 34b, gantry 28b and pedestal (not shown) are identical to the components described above. However, the source 48b and detector 50b are configured differently. In this case, instead of being arranged so that they extend axially from the gantry 28b, the source 48b and detector 30b are arranged such that their lengths essentially traverse the distance between cameras 32b and 34b. Here, detector 50b is mounted on a track 96b via a motor 120b and detector 48b is mounted to a separate track 72b via motor 122b. As best seen in FIG. 8, tracks 72b and 96b are parallel and extend axially from gantry 28b.

At the beginning of an imaging period detector 50b and source 48b are positioned opposite each other at similar ends of corresponding tracks (in FIG. 8 adjacent gantry 28). During imaging, both source 48b and detector 50b are moved in an indexed fashion along their respective tracks in the directions indicated by arrows 124b and 126b to collect transmission data within the imaging area.

Figure 9:
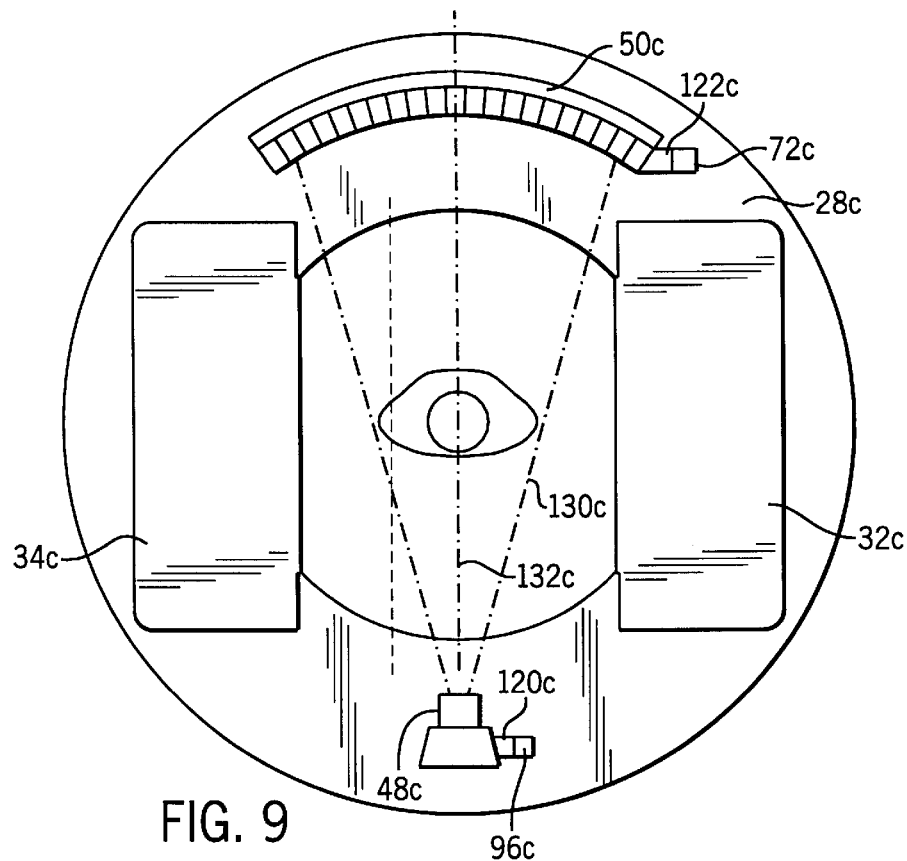
FIG. 9 is a plan view similar to the view of FIG. 3 of a fourth embodiment of the present invention.
Figure 10:
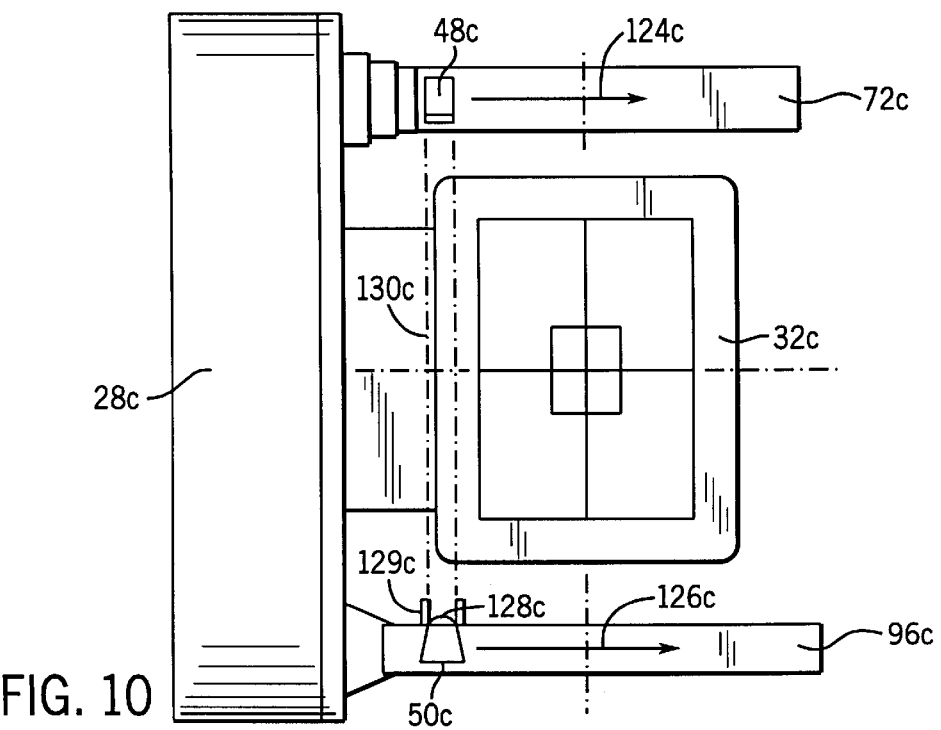
FIG. 10 is a plan view similar to the view of FIG. 4 of the fourth embodiment of the present invention.

Referring now to FIGS. 9 and 10, a fourth embodiment of the invention is illustrated wherein elements identical to the elements shown in the first embodiment are identified by the reference numbers with a "c" thereafter. In this embodiment the two cameras 32c and 34c, gantry 28c and pedestal (not shown) are identical to components described above. However, this source 48c and detector 50c are configured differently. In this case, instead of being a line source, source 48c includes a point source 128c which is collimated via a collimator 129c to form a fan beam 130c which is directed at detector 48c. Collimator 129c collimates the beam 130c in the axial dimension defining a thin axial beam but allows the beam to "fan out" between cameras 32c and 34c such that it subtends essentially the entire length of detector 50c. In addition, instead of being a linear detector, detector 48c is an arcuate detector which forms an arc about point source 128c.

Source 50c is mounted on a track 96c via a motor 120c while detector 48c is mounted on a track 72c via a motor 122c. Source 50c is positioned such that a central ray 132c of fan beam 130c is equispaced from each of cameras 32c and 34c and subtends a central portion of detector 50c. Arcuate detector 48c traverses the distance between cameras 32c and 34c. As best seen in FIG. 10, as with the third embodiment, with this fourth embodiment tracks 72c and 96c extend axially from gantry 28c.

In operation, during imaging periods, both the source 48c and detector 50c are initially positioned so as to oppose each other at similar ends of their corresponding tracks. In FIG. 10, this would be adjacent gantry 28c. During an imaging period, while cameras 32c and 34c receive emission data, the source 48c and detector 50c move together in an indexed fashion along their respective tracks in the directions indicated by arrows 124c and 126c to collect transmission data.

Figure 11:
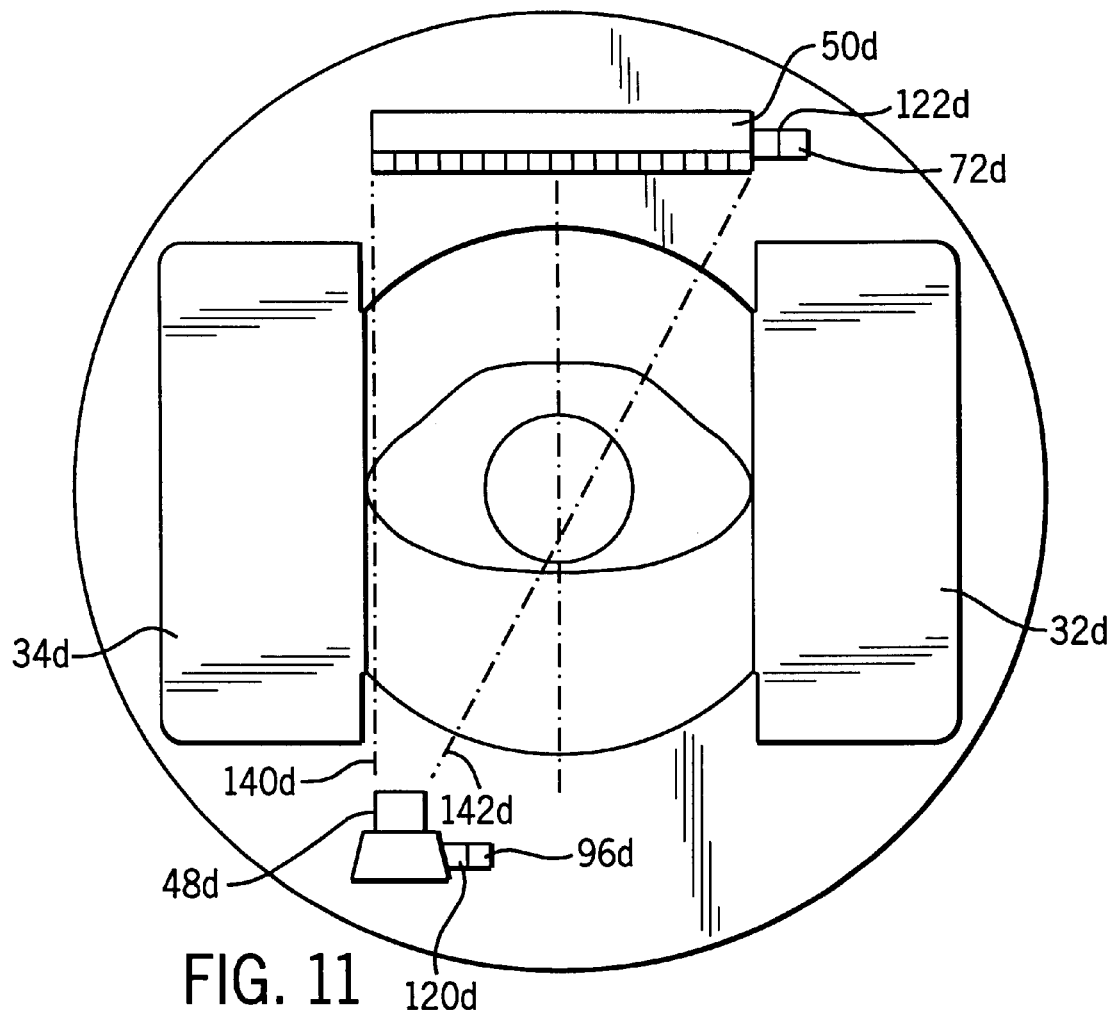
FIG. 11 is a plan view similar to the view of FIG. 3 of a fifth embodiment of the present invention.

Referring now to FIG. 11, a fourth embodiment of the invention is illustrated wherein elements identical to the elements shown in the first embodiment are identified by like referenced numerals with a "d" thereafter. In this embodiment, the two cameras 32d and 34d, gantry 28d and pedestal (not shown) are identical to components described above. However, the source 48d and detector 50d are configured differently. In this case, detector 50d is like detector 50b (FIG. 7) in the third embodiment in that it is linear and mounted to an axially extending track 72d via a motor 122d. However, the source 48d resembles the source 48c (FIG. 9) in the fourth embodiment in that it is a collimated point source, mounted to a track 96d via a motor 120d. However, source 48d is different than source 50c in that the collimator is an asymmetric fan beam collimator which forms a fan beam wherein a first edge defining ray 140d passes through an imaging area parallel to the face of camera 34d and a second edge defining ray 142d, opposite the first edge defining ray 140d, traverses the imaging area on an angle. As well known in the art, this type of asymmetric fan beam provides a greater field of view for transmission of data and also eliminates truncation problems which may be generated via conventional fan beam systems like the one illustrated in FIGS. 9 and 10 and the one illustrated in FIGS. 3 and 4.

In operation, during imaging periods, both source 48d and detector 50d are initially positioned so as to oppose each other at similar ends of their corresponding tracks. During an imaging period, while cameras 32d and 34d receive emission data, the source 48d and detector 50d move together in an indexed fashion along their respective tracks to collect transmission data.

It will be apparent to those of ordinary skill in the art from the above description that many variations are possible from the preferred embodiments. For example, the invention also includes systems wherein the line source 48 is stationary but the detector 50 moves along a track while the source collimator is rotated as a function of the detector position to direct the line transmission towards the detector.

Furthermore, while the invention has been described as one wherein the source 48 and detector 50 are generally disposed at the right angles with respect to the cameras 32 and 34, clearly, the invention would include systems wherein the angle therebetween is not exactly 90°, the important aspect being that neither the source 48 nor detector 50 are positioned between the two cameras 32, 34. Moreover, while the line detector preferably includes only a single row of detectors, the invention clearly includes other detector configurations which have a small number of detector rows. For example, the detector may include 2, 3 or even 5 rows and still provide a cost advantage over other configurations.

In addition, while the invention has been described above in the context of SPECT imaging, the invention could clearly be used to enhance positron emission tomography (PET) imaging in an identical fashion. PET imaging is described in detail in U.S. Pat. No. 5,608,221 entitled MULTI-HEAD NUCLEAR MEDICINE CAMERA FOR DUAL SPECT AND PET IMAGING WITH NONUNIFORM ATTENUATION CORRECTION, which issued to Bertelsen et al. on Mar. 4, 1997. In addition, the present invention could be used with a dual SPECT/PET imaging system like the one described in detail in the above referenced patent. In such a system, for both PET or SPECT imaging, two emission detectors would be oppositely positioned and the transmission source and detector would be positioned on opposite sides of an imaging area.

Furthermore, while the invention is described as including PMT detectors, other types of detectors may be used including solid state CZT, NaI or CSI scintillators using APD technology.

In order to apprise the public of the various embodiments that may fall within the scope of the invention, we make the following claims.

We claim:

1. An apparatus to be used with a planar imaging system including an annular gantry mounted for rotation about a rotation axis, first and second two dimensional detectors mounted on the gantry so as to oppose each other defining an imaging area therebetween, the first and second detectors positioned on first and second sides of the imaging area, respectively, the apparatus for generating and gathering transmission data while the first and second cameras gather emission data, the apparatus comprising:

a detector including an array of N by P photomultiplier tubes where P is less than 5, the detector positioned between the first and second detectors on a third side of the imaging area;

a source positioned between the first and second detectors on a fourth side of the imaging area opposite the detector, the source generating a gamma transmission that is directed at the detector at all times, the detector and source each being correction components, at least one of the correction components being a mobile component;

a motivator for moving the mobile component along a path essentially parallel to the P dimension of the detector and along the side of the imaging area occupied by the mobile component; and a controller for controlling the motivator as a function of gantry angle and time.

2. The apparatus of claim 1 wherein the detector is a line detector.

3. The apparatus of claim 2 wherein the source is a line source and is arranged so that the emission therefrom is parallel to the N dimension of the line detector.

4. The apparatus of claim 1 wherein the source is a point source.

5. The apparatus of claim 4 wherein the source includes a collimator which collimates the gamma emission to form a fan beam which is directed at the detector.

6. The apparatus of claim 5 wherein the collimator is an asymmetric fan beam collimator.

7. The apparatus of claim 1 wherein the P dimension of the detector includes only a single row of detectors.

8. The apparatus of claim 1 wherein the first and second detectors are dual head gamma and positron emission detectors.

9. The apparatus of claim 1 wherein the first and second detectors detect emissions at a first energy level, the detector detects gamma transmissions at a second energy level appreciably different than the first level, and the source generates transmissions at the second energy level.

10. An apparatus to be used with a planar imaging system including an annular gantry mounted for rotation about a rotation axis, first and second two dimensional detectors mounted on the gantry so as to oppose each other defining an imaging area therebetween, the first and second detectors positioned on first and second sides of the imaging area, respectively, the apparatus for generating and gathering transmission data while the first and second cameras gather emission data, the apparatus comprising:

a line detector including an array of N by P photomultiplier tubes where P is less than 5, the detector positioned between the first and second detectors on a third side of the imaging area;

a line source positioned between the first and second detectors on a fourth side of the imaging area opposite the detector, the source generating a gamma transmission that is directed at the detector at all times and is parallel to the N dimension of the line detector, the detector and source each being correction components, at least one of the correction components being a mobile component;

a motivator for moving the mobile component along a path essentially parallel to the P dimension of the detector and along the side of the imaging area occupied by the mobile component;

a controller for controlling the motivator as a function of gantry angle and time; and wherein, one of the correction components is stationary and the apparatus further includes an aligner for rotating the source as the mobile component is moved along the path so as to direct the line transmission toward the line detector at all times.

11. The apparatus of claim 10 wherein the mobile component is the source and the line detector is stationary.

12. The apparatus of claim 11 wherein the line detector is positioned parallel to the axis of rotation.

13. The apparatus of claim 12 wherein the first and second detectors are centered along an imaging axis perpendicular to the axis of rotation and the line detector is positioned along an axis that makes a 90 degree angle with the imaging axis.

14. The apparatus of claim 13 wherein the path is straight and substantially traverses the distance between the first and second detectors along the side of the imaging area occupied by the source.

15. An apparatus to be used with a planar imaging system including an annular gantry mounted for rotation about a rotation axis, first and second two dimensional detectors mounted on the gantry so as to oppose each other defining an imaging area therebetween, the first and second detectors positioned on first and second sides of the imaging area, respectively, the apparatus for generating and gathering transmission data while the first and second cameras gather emission data, the apparatus comprising:

a detector including an array of N by P photomultiplier tubes where P is less than 5, the detector positioned between the first and second detectors on a third side of the imaging area;

a source positioned between the first and second detectors on a fourth side of the imaging area opposite the detector. the source generating a gamma transmission that is directed at the detector at all times, the detector and source each being correction components, at least one of the correction components being a mobile component;

a motivator for moving the mobile component along a path essentially parallel to the P dimension of the detector and along the side of the imaging area occupied by the mobile component;

a controller for controlling the motivator as a function of gantry angle and time; and wherein, both of the correction components are moveable and the motivator is capable of moving one or both of the correction components.

* * * * *